United States Patent
Jiang et al.

(10) Patent No.: US 7,695,601 B2
(45) Date of Patent: Apr. 13, 2010

(54) ELECTROCHEMICAL TEST APPARATUS AND METHOD FOR ITS USE

(75) Inventors: Rongzhong Jiang, Olney, MD (US); Deryn Chu, Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 439 days.

(21) Appl. No.: 11/798,020

(22) Filed: May 9, 2007

(65) Prior Publication Data

US 2007/0261958 A1 Nov. 15, 2007

Related U.S. Application Data

(60) Provisional application No. 60/800,563, filed on May 9, 2006.

(51) Int. Cl.
*G01N 27/26* (2006.01)
(52) U.S. Cl. .......... 204/435; 204/400; 204/412; 204/416; 204/424; 204/433; 422/68.1; 422/82.03; 422/98; 422/104
(58) Field of Classification Search .......... 204/400, 204/412, 416, 424, 433, 435; 422/68.1, 82.03, 422/98, 104
See application file for complete search history.

(56) References Cited

U.S. PATENT DOCUMENTS

| | | | |
|---|---|---|---|
| 3,668,101 A | 6/1972 | Bergman | |
| 3,730,868 A | 5/1973 | Niedrach | |
| 3,742,594 A | 7/1973 | Kleinberg | |
| 3,900,382 A | 8/1975 | Brown | |
| 3,926,766 A | 12/1975 | Neidrach, et al. | |
| 3,957,612 A | 5/1976 | Niedrach et al. | |
| 3,957,613 A | 5/1976 | Macur | |
| 4,419,210 A | * 12/1983 | Wang | 204/403.05 |
| 4,488,938 A | * 12/1984 | Jirovsky et al. | 205/791 |
| 4,534,355 A | 8/1985 | Potter | |
| 4,585,542 A | * 4/1986 | Wright et al. | 204/415 |

(Continued)

OTHER PUBLICATIONS

Reddington, et al., "Combinatorial Electrochemistry: A Highly Parallel, Optical Screening Method for Discovery of Better Electrocatalysts," Science, (Jun. 12, 1998):vol. 280. No. 5370, pp. 1735-1737.

(Continued)

*Primary Examiner*—Bruce F Bell
(74) *Attorney, Agent, or Firm*—William V. Adams; Lawrence E. Anderson (57) ABSTRACT

An electrochemical electrode probe includes an elongated body of a porous material disposed in a housing. The porous material is permeated with an electrolyte. A body of electrode material surrounds the porous body and functions as one electrode of an electrochemical system. A portion of the elongated body of porous material projects beyond the electrode body and functions to establish ionic and electrical conductivity with a sample of material which is to be tested. The sample of material functions as a working electrode, and the electrode body of the probe functions as a counter electrode/reference electrode. Further disclosed is an electrochemical analysis system which includes the probe and a support plate operable to retain a plurality of samples of test material thereupon. The probe is moved across the plate to sequentially measure the electrochemical properties of the various samples of material. Also disclosed are methods for using the system.

20 Claims, 4 Drawing Sheets

U.S. PATENT DOCUMENTS

| | | | |
|---|---|---|---|
| 4,753,719 | A | 6/1988 | Yamaguchi et al. |
| 4,861,454 | A | 8/1989 | Ushizawa et al. |
| 5,030,336 | A * | 7/1991 | Koch .................. 204/415 |
| 5,120,421 | A | 6/1992 | Glass et al. |
| 5,223,123 | A * | 6/1993 | Koch .................. 204/415 |
| 5,431,806 | A | 7/1995 | Suzuki et al. |
| 5,486,279 | A * | 1/1996 | Friese et al. ............ 204/429 |
| 5,834,195 | A | 11/1998 | Benkovic et al. |
| 5,880,972 | A | 3/1999 | Horlbeck |
| 5,951,846 | A | 9/1999 | Lewis et al. |
| 6,004,617 | A | 12/1999 | Schultz et al. |
| 6,132,971 | A | 10/2000 | Thorp et al. |
| 6,187,164 | B1 | 2/2001 | Warren et al. |
| 6,372,105 | B1 | 4/2002 | Saito et al. |
| 6,692,856 | B2 | 2/2004 | Smotkin |
| 6,756,109 | B2 | 6/2004 | Warren et al. |
| 6,758,951 | B2 | 7/2004 | Giaquinta et al. |
| 6,818,110 | B1 | 11/2004 | Warren et al. |
| 6,913,849 | B2 | 7/2005 | Mallouk et al. |
| 7,074,318 | B1 | 7/2006 | Chu et al. |
| 2008/0226961 | A1 * | 9/2008 | Jiang et al. ............ 429/33 |

OTHER PUBLICATIONS

Jiang, R. et al. "A combinatorial approach toward electrochemical analysis," Journal of Electroanalytical Chemistry, 527 (1-2) 137-142 (2002) *.

Jiang, et al. "Combinatorial Approach toward High-Throughput Analysis of Direct Methanol Fuel Cells," J. Comb. Chem., Jan. 2005,7 (2), pp. 272-278.

Baker, et al., "Membrane Separation Systems: Recent Developments and Future Directions" Noves Data Corporation Park Ridge, New Jersey, U.S.A. (1991) p. 344. *.

Strasser, et al., "High Throughput Experimental and Theoretical Predictive Screening of Materials—A Comparative Study of Search Strategies for New Fuel Cell Anode Catalysts," J. Phys. Chem. B, 2003,107 (40), pp. 11013-11021 *.

Sullivan, et al. "Automated Electrochemical Analysis with Combinatorial Electrode Arrays,"Anal. Chem., (1999), 71 (19), pp. 4369-4375. *.

Guerin, et al., "Combinatorial Electrochemical Screening of Fuel Cell Electrocatalysts," J. Comb. Chem., (2004), 6 (1), pp. 149-158 *.

Caplus Abstract of Terry, "Electrolytic estimation of arsenic," Midland Druggist and Pharmaceutical Review (1919), 53, 132-3. *.

Caplus Abstract of Gelfayan, G., "Electrolytic reduction methods in analytical chemistry, VIII, Qualitative test for tungsten," Izvest. Akad. Nauk armyan. S.S.R., Fiz.-Mat., Estestven. i Tekh. Nauki (1950), 3, 523-6. *.

Chu et al., "Methanol Electro-oxidation n Unsupported Pt-Ru Alloys at Different Temperatures," J. Electrochem, Soc. 143 (1996): 1685-1690. *.

Pollack et al., "Selective Chemical Catalysis by and Antibody." Science, (Dec. 19, 1986) 234, 1570.

Surampudi et al., "Advances in Direct Oxidation Methanol Fuel-Cells." Journal of Power Sources, 47 3rd ser. (1994): 377-385. *.

Ren et al., "High Performance Direct Methanol Polymer Electrolyte Fuel Cells," Electrochemical Society 143 (1996). *.

Xiang et al., "A Combinatorial Approach to Materials Discovery," Science, (Jun. 23, 1995): 1738-1740.

* cited by examiner

ELECTROCHEMICAL TEST APPARATUS AND METHOD FOR ITS USE

RELATED APPLICATION

This application claims priority of U.S. Provisional Patent Application Ser. No. 60/800,563 filed May 9, 2006, entitled "Movable Electrode/Electrolyte Probe for High Throughput Electrochemical Analysis."

GOVERNMENT INTEREST

The invention described herein may be manufactured, used, and licensed by or for the United States Government.

FIELD OF THE INVENTION

This invention relates generally to electrochemical testing systems and methods; more particularly, it relates to electrochemical devices and methods for the high throughput analysis of electrode materials. In particular aspects, this invention relates to an apparatus including a particularly configured electrode/electrolyte probe, and an electrode array containing a large number of discrete working electrodes, as configured and operative to comprise an electrochemical system for the high throughput analysis of electrochemical materials.

BACKGROUND OF THE INVENTION

There is a need for a system and method whereby large numbers of materials, and combinations of materials, may be rapidly and accurately scanned so as to determine their performance as components of electrochemical devices such as fuel cells, batteries, chemical reactors, catalytic systems and the like. Various systems for such high throughput scanning have been shown and suggested in the prior art. For example, the use of a combinatorial approach to study electrochemistry was first reported by Reddington et al., Ref. Science, 280, 1735 (1998). As disclosed, an array of material spots disposed on a large, flat working electrode of an electrochemical cell was prepared. As shown therein, an optical screening method was used to determine proton concentration within small active portions of the array. Such optical scanning methods are inherently limited because the variation of proton concentration is not easily detectable within the small areas of material spots in concentrated base and acid electrolytes. Other such combinatorial mass screening systems are known in the art. In one approach, a large container is employed to encompass a counter electrode, a reference electrode, and an array of material samples disposed upon multiple working electrodes. Such systems are shown, for example, in U.S. Pat. Nos. 6,187,164; 6,756,109; 6,818,110; and 6,132,971. In other similar systems, the multiplicity of materials being tested are disposed on a single working electrode, and such a system is shown in U.S. Pat. No. 6,913,849. In another approach of the prior art, a number of small containers are used to provide an array of electrochemical cells disposed upon a single flat base. Multiple electric leads are printed on the base and disposed to conduct electricity from each test sample to an analyzer. Such a system is shown in U.S. Pat. No. 6,758,951. In yet another type of system as embodied in U.S. Pat. No. 6,692,856, an array of sensor electrodes are inserted into a number of separate holes in an anode base configured to hold individual sensor electrodes. Further portions of the disclosed apparatus include a common counter electrode and a polymer membrane disposed between the sensor electrodes and the counter electrode. All of the foregoing apparatus are very complex in mechanical configuration and operation and typically require multiple, printed electrical leads. This leads to complicated operation in the devices which decreases any benefit obtained from large scale scanning systems.

Another approach to providing for the large scale scanning of a plurality of samples is disclosed in U.S. Pat. No. 7,074,318 which was filed by the inventors hereof, the disclosure of which is incorporated herein by reference. The prior art system described in the above-referenced patent describes a system for screening a plurality of materials disposed, in an array configuration, upon a common substrate. These samples are all in electrical communication with the substrate, which in turn is connected to an electrochemical analyzer. In a typical implementation, the substrate plate is covered with an electrically insulating layer having a plurality of openings formed therein, and the samples being tested are exposed in the openings. In this manner, the samples are all connected to the substrate, but are spaced from one another by the insulating, upper coating.

The system of the U.S. Pat. No. 7,074,318 patent further includes a large area counter electrode assembly which is separated from the substrate and associated array of test samples. This counter electrode assembly is in electrical communication with the analyzer. A relatively long, typically flexible, ionically conductive member, referred to as ionic conductive wire, is used to provide electrical and ionic conductivity between the counter electrode and selected members of the array. When such ionic conductivity is established, the selected member of the array and the counter electrode form an electrochemical cell, and the analyzer may be used to analyze the electrochemical properties of that resultant cell. By moving the ionically conductive wire from one member of the array to another, the entire array may be sequentially scanned. The ionic resistance of the ionically conductive wire is relatively high; therefore, only a very small current, typically less than 1 mA, can be measured by the apparatus of the prior art. This greatly restricts the utility of the system and the nature of the measurements which may be made thereby.

As will be apparent from the following, there is a need for a system which allows for the high speed, simple, and accurate measurement of electrochemical properties of a plurality of test samples.

SUMMARY OF THE INVENTION

Disclosed herein is an electrochemical apparatus for scanning a plurality of test samples. The apparatus includes a support plate comprised of a material which is electrically conductive but not ionically conductive. The plate is configured and operable to have a plurality of test samples supported thereupon in a spaced-apart relationship, in electrical communication with the plate. The apparatus includes a test probe. The probe comprises a housing with a porous body disposed in the housing. The porous body has a tip portion which projects from the housing. An electrolyte material is retained in the porous body, and the body of electrode material is in electrical communication with the porous body via the electrolyte. When the projecting tip portion of the porous body is placed in contact with a test sample supported on the plate, the electrolyte establishes electrical and ionic communication between the sample and the body of electrode material so as to form an electrochemical cell wherein the test sample constitutes a working electrode of the cell and the body of electrode material constitutes a counter electrode/ reference electrode of the cell. An electrochemical analyzer in communication with the sample and the electrode material of the probe will determine electrochemical properties of the material being tested.

In particular instances, the apparatus may include discrete bodies of electrolyte material in contact with each of the samples supported on the plate, and this electrolyte material may be retained in a porous material such as a porous polymer. The support plate may include a body of electrically insulating material disposed thereupon, which body includes a number of openings for receiving the test samples. In particular instances, the support plate is comprised of graphite.

In specific embodiments, the probe may include a porous body of an electrochemically inert, electrically conductive material in electrical contact with the body of electrode material, and this porous, electrochemically inert material may comprise a foamed metal. The electrode body of the probe may further include a catalytic material or the like supported thereupon.

In particular embodiments, the surface area of the body of electrode material in the probe is selected so as to be significantly larger in area than is the contact area between the probe tip and any of the test samples. In specific instances, the area of the probe material is at least five times greater than the surface area of the test sample being contacted. In particular instances, the relative areas of the probe electrode material and the contact area between the probe and the sample constituting the working electrode is selected so that in the operation of the system, the counter electrode/reference electrode formed by the probe electrode is not polarized.

Also disclosed herein are specific probe structures and methods for the use of the probe and the system.

DESCRIPTION OF THE PREFERRED EMBODIMENTS

The present invention is directed to systems, components and methods for rapidly screening large numbers of materials to determine their electrochemical activity, as for example their activity as battery materials, fuel cell materials, catalysts and the like. The system of the present invention is operable to measure performance of electrochemical cells at relatively high currents, typically at least 100 mA. Thus, the system of the present invention is capable of acquiring a wide range of diverse data regarding the materials.

Figure 1:
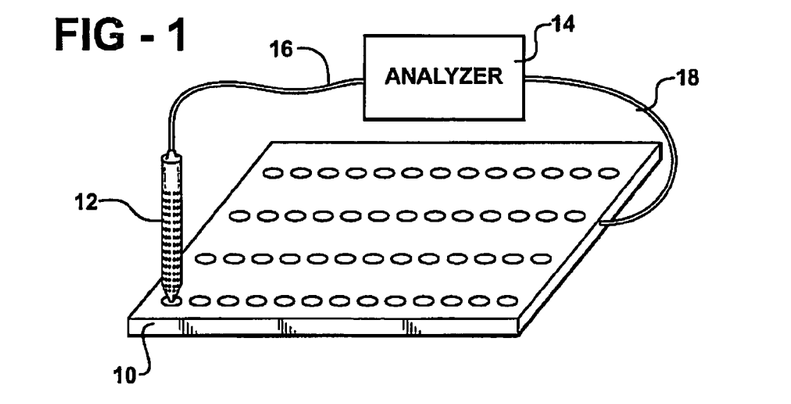
FIG. 1 is a perspective view of a general system of the present invention.

Referring now to FIG. 1, there is shown one embodiment of an electrochemical apparatus in accord with the present invention as employed for measuring electrochemical properties of a plurality of samples. The apparatus of FIG. 1 includes a support plate 10 comprised of a material which is electrically conductive but not ionically conductive. As will be explained in detail below, the plate is configured to have a plurality of test samples supported thereupon in a spaced-apart relationship, in electrical communication with the plate. The apparatus of FIG. 1 further includes a test probe 12. In the illustrated embodiment, the probe 12 is configured as a generally cylindrical probe of the approximate size and shape of a writing instrument. It will thus be appreciated that in the use of the system of FIG. 1, an operator can move the probe to various locations on the support plate. Details of the probe and plate will be given below. In the FIG. 1 embodiment, the probe 12 is in electrical communication with an electrochemical analyzer 14 by means of an electrical lead 16, and the support plate 10 is likewise in electrical communication with the analyzer 14 by a second lead 18. These leads are electrically conductive; but unlike the prior art system described above, the leads need not be ionically conductive. The analyzer may be any type of electrochemical analyzer known in the art, as adapted to measure electrochemical potentials or other such properties of an electrochemical cell.

Figure 2:
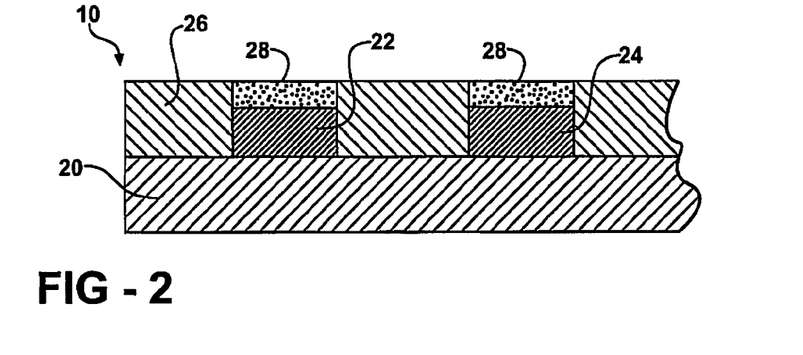
FIG. 2 is a cross-sectional view of a portion of the support plate of the system of FIG. 1.

Referring now to FIG. 2, there is shown a cross-sectional view of a portion of the support plate 10 of FIG. 1. As illustrated, the plate 10 includes a body 20 of a material which is electrically conductive but not ionically conductive, as well as electrochemically and chemically inert to samples being tested, and to other components of the apparatus. There are a variety of materials which meet these criteria. One material having utility in the present invention comprises carbon, specifically graphite. Graphite is inert, has good electrical conductivity, is not ionically conductive, and it is inert to most species. Other materials which meet these criteria include metals, and some specific examples of such metals are ferrous metals such as stainless steel and other alloys, titanium, and noble metals, among others.

As illustrated in FIG. 2, the plate 10 has a number of samples of a test material, in this instance samples 22 and 24, disposed thereupon. These samples may comprise any type of material such as an alloy, catalyst, composite or other material which is to have its electrochemical properties evaluated. In the illustrated embodiment, a sheet of electrically insulating material, such as a sheet of fluoropolymer material 26, is disposed upon the conductive body 20. The insulating material has a plurality of openings defined therein, and the test samples are disposed within these openings. It is to be noted that the insulating layer 26 is optional, and in some instances, sample materials may be simply placed upon the conductive body 20. Placing the samples may be accomplished by any technique known in the art including vapor deposition coatings, solvent coatings, or by directly applying the materials as for example in a slurry form thereto.

In the illustrated embodiment of FIG. 2, each of the samples 22, 24 have a body of porous material 28 disposed there atop. This porous material is, in the use of the system, wetted with an electrolyte material and serves to foster the establishment of electrical conductivity to the samples. Again, this feature of the invention is optional. Typical materials for comprising the porous body 28 will include porous polymeric materials of the type used as separators in electrochemical cells.

In the system of the present invention, all of the function of the counter electrode/reference electrode is disposed within the probe 12, and the connection of the probe 12 to the analyzer need only be an electrical connection, and there is thus no long range ionic conductor required. This feature greatly lowers the ionic resistance of the system and permits operation at relatively high current levels, typically 100 times higher than prior art systems of the type described above. Typical currents used in the operation of the system of the present invention are in the range of 100 mA.

Figure 3:
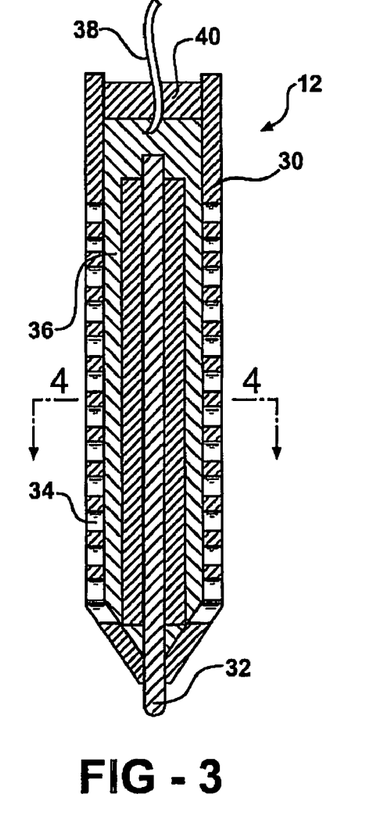
FIG. 3 is a longitudinal cross-sectional view of a probe of the present invention.

Referring now to FIG. 3, there is shown a cross-sectional view of the probe 12 shown in FIG. 1. As noted above, this probe is of an approximately pen shape, and it contains an electrode system, electrolyte and appropriate electrical conductors. The probe 12 provides a very large electrode area relative to the sample area; therefore its potential will not appreciably change with time. Therefore, the counter electrode provided by the probe also functions as a reference electrode. It is a notable feature of the present invention that the relative areas of the active electrode portion of the probe 12 are significantly greater (at least five times greater) than the corresponding active area of the sample being tested. These areas are selected so that in the operation of the system, the counter electrode of the probe is not polarized. This type of geometric arrangement is in contrast to typical electrochemical cells wherein the working electrode and the counter electrode are in a sandwich relationship and have the same area; and hence, polarization must be taken into account, and a separate reference electrode will be required. In the present invention the counter electrode has a very large surface area and the contact area between the electrode/electrolyte probe and the working electrode which is constituted by the sample being tested is quite small (typically 0.2 cm$^2$).

Figure 3B:
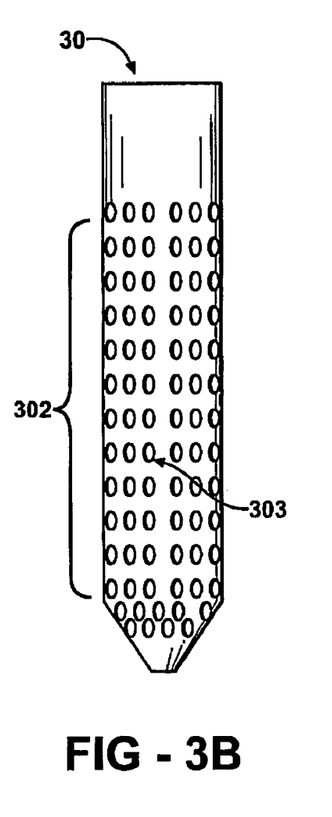
FIG. 3B is a side, perspective view of the housing of the probe of FIG. 3.

As will be seen from FIG. 3, the electrode/electrolyte probe includes a generally cylindrical, elongated housing 30 formed from an electrically insulating material such as a polymer. FIG. 3B is a side view of the housing 30, and it shows that a lowermost portion 302 of the housing 30 includes a plurality of holes 303 defined therethrough. These holes 303 permit passage of air, so that oxygen may reach the electrode components of the probe assembly. In the illustrated embodiment, the perforated portion 302 of the housing 30 is approximately 5 cm in length, and the total length of the housing is about 8 cm. Other lengths may be employed. Also, in other embodiments, passage of air through the housing may be provided for by slots, as well as by the use of porous materials for the housing.

A porous body of material is disposed in the housing in a generally concentric relationship therewith. This porous body 32 is, in the use of the system, permeated with an ionically conductive electrolyte. The nature of the electrolyte will depend upon particular applications, and typical electrolytes include aqueous solutions of potassium or sodium hydroxide, typically at 30% w/w concentrations; salts such as potassium sulfate, which is typically employed at a 10% w/w concentration; or acids such as sulfuric acid at a 1 molar concentration. The porous body 32 is typically comprised of a polymeric sponge material which in particular embodiments is a hydrophilic polymer such as polyurethane. In other instances, the porous body may be a relatively rigid material such as a porous body of ceramic. Disposed in a concentric relationship with at least a portion of the length of the porous body 32 is a body of electrode material 34. This body of electrode material 34 functions as the counter electrode/reference electrode, and is in the illustrated embodiment comprised of a body of electrically conductive, air permeable, porous material such as a carbon cloth. As is known in the art, such carbonized cloth may comprise carbonized cotton, a carbonized polymer, or a carbonized polyester-carbon cloth. Depending upon the particular electrochemical evaluations being conducted, the electrode body 34 may include further electroactive materials. For example, the electrode body 34 may be an $O_2$ electrode as will be used for the study of fuel cells and metal/air batteries. In such instance, the electrode 34 will include a reducing catalyst thereupon. This catalyst material may be coated onto the porous carbon fabric, and some such catalysts include platinum black, platinum, cobalt oxides, nickel oxide, iron compounds such as iron porphyrins, other organometallics such as cobalt porphyrins and the like. In yet other applications, different catalysts may be employed. In general, any electrode system of the prior art may be adapted to the illustrated configuration.

As is further shown in FIG. 3, a porous, inert, electrically conductive body of metal foam 36 is disposed in the probe so as to be in a concentric relationship with the electrode body 34 and the porous electrode body 32. The porous, metal foam establishes electrical contact to an electrical lead 38, which in turn establishes electrical communication with the analyzer device. The metal foam also serves to allow air to permeate through the electrode probe structure. In those instances where electrochemical reactions not requiring presence of air or other gases are being evaluated, the porous structures of the FIG. 3 embodiment need not be employed. The metal foam, if employed, may be comprised of any metal which is inert to the electrochemical reactions and has good electrical conductivity. Such metal foams include nickel foam, titanium foam, platinum foam and gold foam. Likewise, the material of the electrical lead 38 is chosen so as to be inert and compatible with the use and function of the probe. Again, similar metals may be used to manufacture the lead. As is further shown in FIG. 3, a body of electrically insulating material 40 is disposed so as to seal the top of the probe. This material may comprise any type of polymer, as well as any other electrically insulating material such as natural or synthetic rubber.

Figure 4:
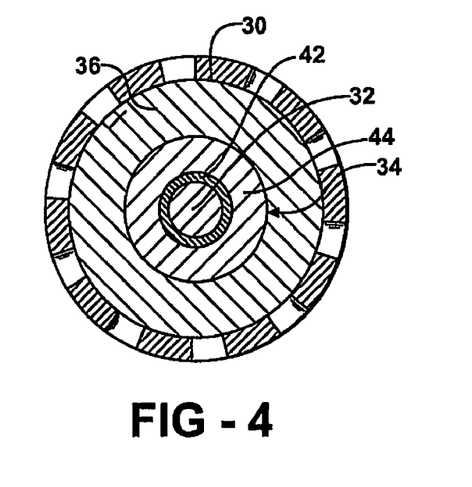
FIG. 4 is a cross-sectional view of the probe of FIG. 3 taken along line 4-4.

Referring now to FIG. 4, there is shown a cross-sectional view of the probe of FIG. 3 taken along line 4-4. FIG. 4 shows the concentric relationship of the components, specifically illustrating the porous core 32 and the electrode body 34. As is shown in FIG. 4, the electrode body 34 includes a coating of platinum catalyst 42 disposed upon a body of porous carbon cloth 44. FIG. 4 further shows the porous metal body 36 and the housing 30.

In one specific embodiment of probe, the dimensions of the body of metal foam are approximately 20 mm by 80 mm by 2 mm; the carbon cloth has dimensions of 20 mm by 50 mm by 0.3 mm, and it bears a catalyst coating supported thereupon having dimensions of 20 mm by 40 mm by 0.010 mm. In this embodiment, the area of the electrode of the probe is approximately 8 cm$^2$. The final diameter of the probe is about 1.27 cm. The length of the cone tip exposed outside of the housing is approximately 0.5 cm, which ensures a low IR (current× resistance) drop for a high current response. The total length of the cylindrical sponge is approximately 5 cm so as to furnish a reservoir of electrolyte. In the use of a system of the present invention, the leads from the probe and support plate are connected to an electrochemical analyzer such as a potentiostat, galvanostat, a battery test station or an electronic load. The lead of the electrode/electrolyte probe links to the positive terminal of the instrument and the electrode array to the negative terminal. High throughput analysis of sample materials may be carried out by moving the tip of the electrode/electrolyte probe onto the top of each sample comprising a working electrode and measuring the current and potential produced thereby. In a system of this type, each measurement may be made in a relatively short time (typically 35 seconds).

The present invention will be described with reference to specific examples as set forth below.

General Procedure

Chemicals and Materials: Pure, fine, elemental, metal powders of zinc and copper were purchased commercially. High purity graphite plates were obtained from SGL Carbon Corp., and used for processing arrays of anode electrodes for zinc/air batteries. The porous, electrolyte-retaining separator material on the working electrodes was commercial hydrophilic polyestersulfone filter paper with 0.45 μm pore size. High surface area platinum black was purchased from Johnson Matthey Company for the oxidation catalyst. 5% Nafion solution was purchased from Aldrich Chemical Company for use as a binder for the metal powders. Nickel foam having a 2 mm thickness was purchased from Marketech International Company.

Working Electrode Array: The working electrode array was prepared from a flat graphite plate having a Teflon sheet affixed thereto to form an insulating surface. The Teflon sheet was tailored into many holes to expose a number of uncovered graphite areas for forming a working electrode array. Each working electrode had $0.196 \text{ cm}^2$ area and each was separated by 1.0 cm from others. These electrodes were electrically shorted but ionically insulated. Because these electrodes were isolated by a Teflon cover, the liquid electrolyte volumes on each electrode cannot contact each other. Zinc and copper powders were mixed and coated on the working electrode with 5% Nafion as a binder, and then dried at 40° C. The surfaces of materials on the working electrodes were covered with hydrophilic polyestersulfone filter paper as separators. The separators were rinsed with 30% potassium hydroxide.

$O_2$-Electrode/Electrolyte Probe: The pen shape $O_2$-electrode/electrolyte probe consisted of four main parts. The most inner part was an electrolyte core (5 cm in length), and terminated with a cone tip (0.5 cm in length), which was made with a hydrophilic polymer foam. A solution of 30% potassium hydroxide was used as the electrolyte. A sheet of $8 \text{ cm}^2$ carbon cloth was used as gas diffusion electrode body. Platinum catalyst was coated on the carbon coating (loading 2 $mg/cm^2$) for catalytic oxygen reduction. The outermost part was nickel foam used as a current collector and also as a secondary gas diffusion layer. The layers of carbon cloth and nickel foam were tightly combined around the electrolyte core. The outer part of the probe was a plastic handle (1.3 cm in diameter) and an electric lead linked to the metal foam.

Example 1

Figure 5:
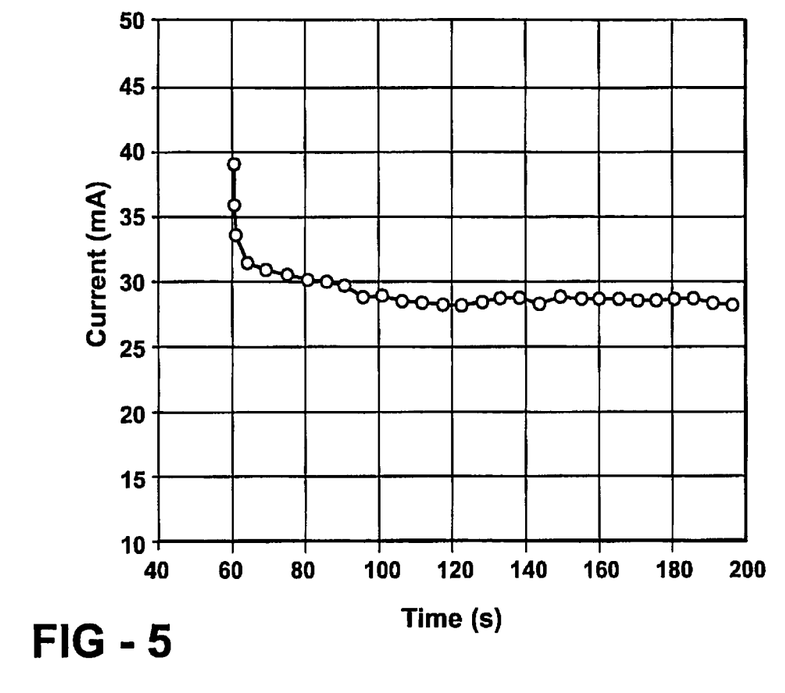
FIG. 5 is a graph showing current variation of a zinc/air battery at constant voltage, as a function of time, as measured utilizing an electrode probe of the present invention.

The first experiment was to examine the response time by a potential step method. The $O_2$-electrode/electrolyte probe linked a zinc electrode in the working electrode array to form a zinc/air battery. The cell had an open circuit voltage about 1.5 V. The potential was stepped to 1.0 V from the open circuit voltage, and discharge current was generated and decreased slowly until reaching 28 mA. FIG. 5 shows the current variation obtained by applying a potential of about 1.0 V. About 35 seconds was needed to obtain a stable discharge current, which implies that the screening rate of the $O_2$-electrode/electrolyte probe is 35 second per material sample.

Example 2

Figure 6:
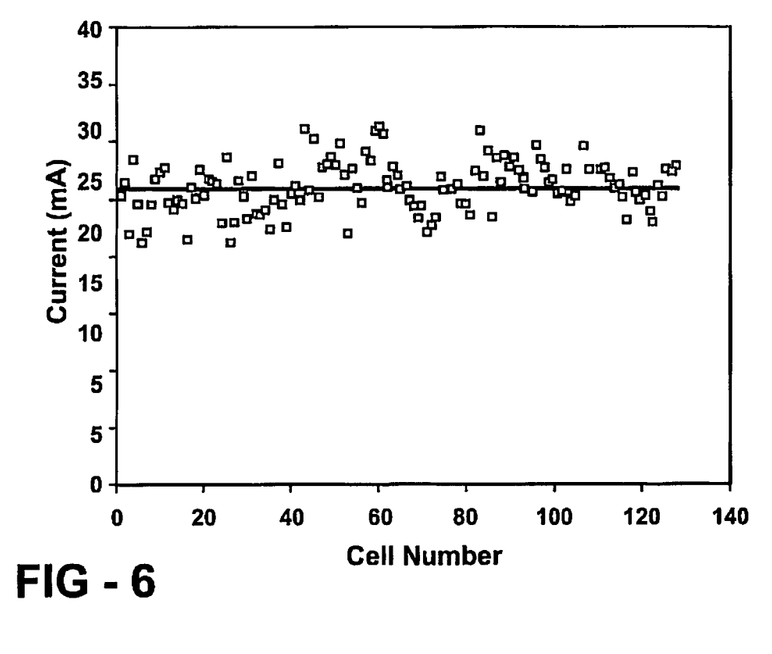
FIG. 6 is a graph showing the results of the current distribution of 128 zinc/air cells measured using the system of the present invention.

An array of zinc electrodes was analyzed using the $O_2$-electrode/electrolyte probe. The coating on each working electrode was about $10\pm2$ mg by weight. FIG. 6 shows the current distribution of the 128 zinc/air cells at a potential of 1.0 V. These data are varying with deviations of $\pm5$ mA around the mean value (26 mA). The maximum deviation is up to 19%, which is consistent with the 20% weight deviation of zinc material coated on the working electrode in the electrode array.

Example 3

Figure 7:
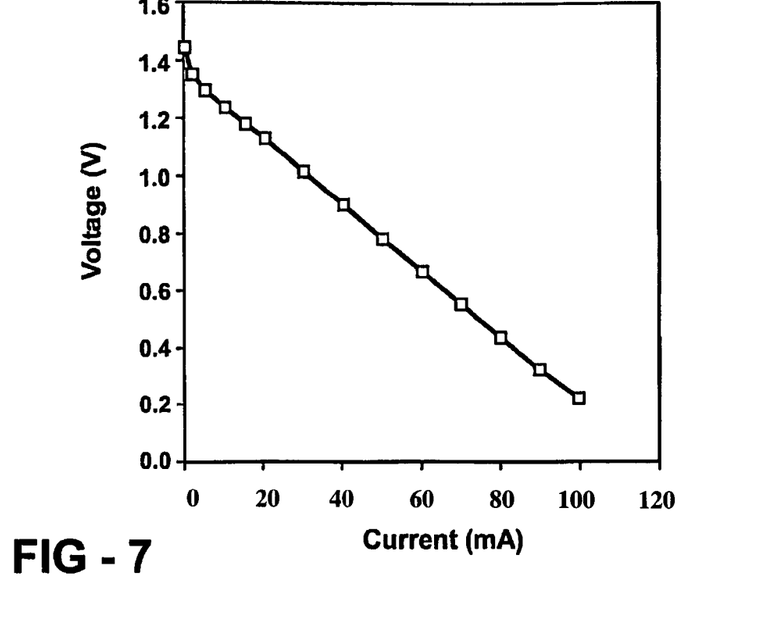
FIG. 7 is the voltage current curve for a zinc/air battery obtained using the methods of the present invention.

An electrochemical polarization curve can be measured using the $O_2$-electrode/electrolyte probe, as long as it links a zinc electrode in the working electrode array to form a zinc/air cell (here the $O_2$-electrode/electrolyte probe acts as the air electrode). FIG. 7 shows a polarization curve of a zinc/air cell obtained with the combinatorial method. The open circuit voltage is 1.5 V. A method of multiple-small-potential-steps was applied to gradually decrease the cell voltage in order to obtain the discharge current. It is a typical polarization curve, and we can see two parts of kinetic controlled and Ohmic controlled electrochemical processes. The low current region (current<10 mA) belongs to the kinetic controlled process. When the current is greater than 10 mA, the polarization curve becomes a straight line. The high current region (current>10 mA) belongs to the Ohmic controlled process. The current value is up to 100 mA at 0.2 V that is limited by the zinc electrode area ($0.196 \text{ cm}^2$). Apparently, the upper current-limit of the electrode-probe is larger than 100 mA. This current limit is good enough for combinatorial electrochemistry because the area of one electrode is small enough ($0.196 \text{ cm}^2$).

Example 4

Figure 8:
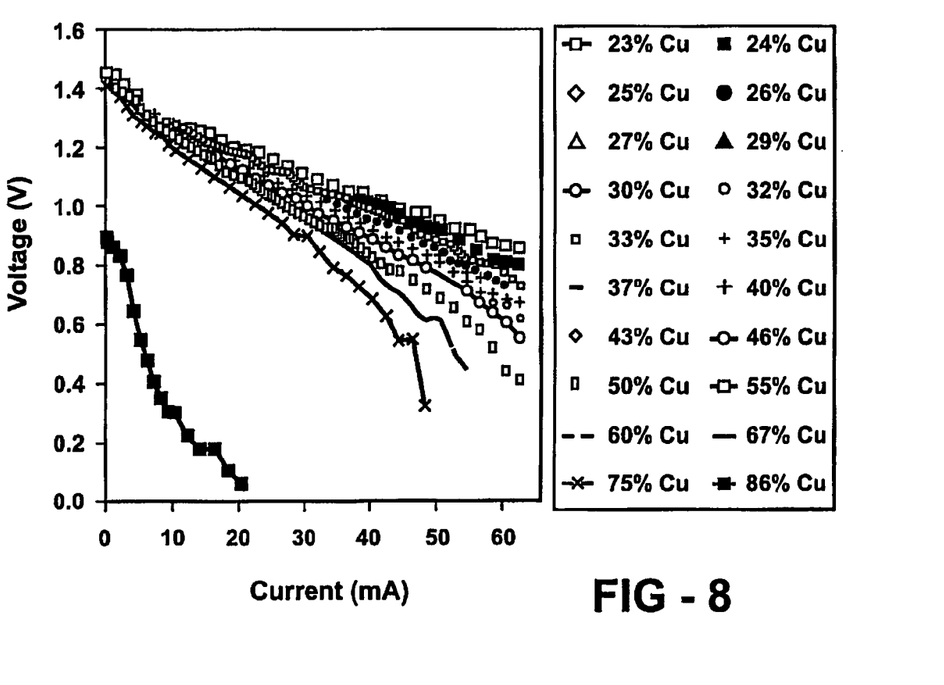
FIG. 8 is a series of voltage current curves for a 20 member array of zinc/air batteries as measured using the system of the present invention.
Figure 9:
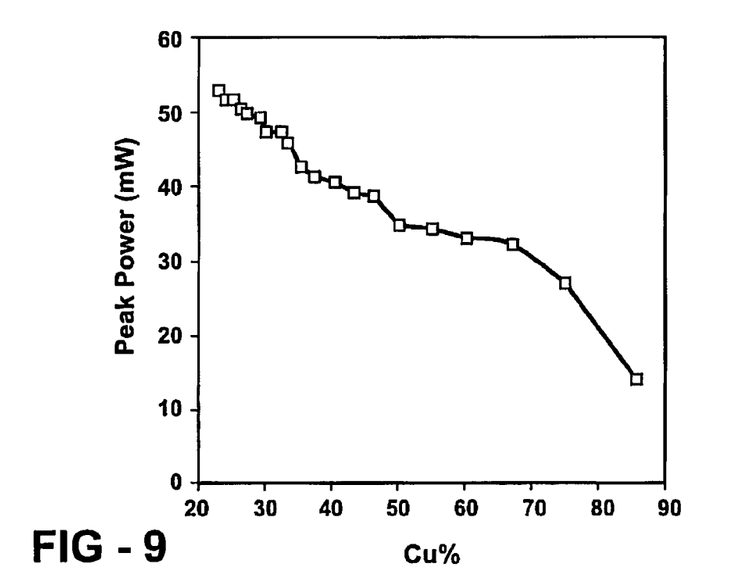
FIG. 9 is a graph of peak power versus copper percentage for the anode materials of FIG. 8.

The $O_2$-electrode/electrolyte probe was further examined by screening of a 20 member array of copper supported zinc/air battery (ZnCu/air). In a zinc/air battery there is a common problem of zinc electrode's volume change during discharge time, which leads to a loss of electric conductivity between the anode material and the current collector. We tried to use copper as an anode supporter to obtain better electric contact among the zinc particles during discharge. Copper (Cu) is a well known element that forms an alloy with zinc. FIG. 8 shows polarization voltage-current curves of a 20 member of ZnCu/air batteries screen by the $O_2$-electrode/electrolyte probe. These batteries have about the same open circuit of 1.4 V. The Cu content in the ZnCu electrode affects the discharge performance significantly. With increasing the percentage of Cu the discharge voltage decreases appreciably for each of given discharge current. If the content of Cu is higher than 86%, both of the voltage and current is decreased remarkably. FIG. 9 shows the plot of the battery's peak power versus Cu percentage in the anode obtained from the data of FIG. 8. The peak power shifts with Cu content about linearly. Therefore, we need to use only minimum amount of Cu to achieve the best electric conductivity and avoid significant decrease in discharge power and energy density.

From the foregoing, it will be appreciated that the present invention provides for a novel electrode probe which includes a high surface area electrode therein. The probe is configured as a pen-shaped item, and may be utilized in an electrochemical analyzer system of the present invention in connection with a support plate having a plurality of samples thereupon. The samples function as working electrodes, and the probe provides counter electrode/reference electrode function. The system may be implemented in various configurations, and may be used to analyze various electrochemical properties.

The system of the present invention allows for the rapid scanning of electrode materials, catalysts, and other components of electrochemical systems. In view of the foregoing, it is to be understood that numerous modifications and variations of the present invention may be implemented. The foregoing drawings, discussion and description are illustrative of some specific embodiments but are not meant to be a limitation upon the practice of the invention. It is the following claims, including all equivalents, which define the scope of the invention.

The invention claimed is:

1. An electrochemical apparatus for scanning a plurality of test samples, said apparatus comprising:
   a support plate comprising a material which is electrically conductive but not ionically conductive, said plate being configured and operable to have a plurality of test samples supported thereupon in a spaced apart relationship, in electrical communication with said plate;
   a test probe, said test probe comprising: a housing; a porous body disposed in said housing, said porous body having a tip portion projecting from said housing; an electrolyte material retained in said porous body; and a body of electrode material which is in electrical communication with the porous body via the electrolyte;
   wherein when said projecting tip portion of said porous body is placed in contact with one of said plurality of test samples, said electrolyte establishes electrical and ionic communication between said sample and said body of electrode material so as to form an electrochemical cell, wherein said test sample constitutes one electrode of said electrochemical cell and said body of electrode material constitutes the other electrode of said electrochemical cell; and whereby, said electrochemical cell may be analyzed by an analyzer which is in electrical communication with said test sample and said electrode material of said probe.

2. The electrochemical apparatus of claim 1, wherein when test samples are disposed upon said support plate, said apparatus includes a discrete body of electrolyte material in contact with each sample.

3. The electrochemical apparatus of claim 2, wherein said discrete bodies of electrolyte material are each retained in a porous member associated with a respective test sample.

4. The electrochemical apparatus of claim 1, wherein said support plate includes a body of electrically insulating material disposed thereupon, said body of electrically insulating material having a plurality of openings defined therein, wherein said test samples may be disposed in said openings.

5. The electrochemical apparatus of claim 1, wherein said support plate is comprised of graphite.

6. The electrochemical apparatus of claim 1, wherein said probe further includes a porous body of an electrochemically inert, electrically conductive material in electrical contact with said body of electrode material.

7. The electrochemical apparatus of claim 1, wherein said electrode material comprises a support body having an electrochemically active material disposed thereupon.

8. The electrochemical apparatus of claim 7, wherein said support body is porous.

9. The electrochemical apparatus of claim 7, wherein said support body is electrically conductive.

10. The electrochemical apparatus of claim 1, wherein the housing of said probe is an elongated, cylindrical member, and said porous body extends along at least a portion of the length of the cylindrical member, and said body of electrode material is in a coaxial relationship with said porous body.

11. The electrochemical apparatus of claim 1, wherein the surface area of said body of electrode material in the probe is larger in area than is each of said test samples.

12. The electrochemical apparatus of claim 11, wherein the surface area of said body of electrode material in said probe is at least five times greater than the surface area of any of said test samples.

13. The electrochemical apparatus of claim 11, wherein when said porous body is placed in contact with one of said plurality of test samples so that said electrochemical cell is formed, the electrode constituted by said test sample is polarized, and the electrode constituted by said electrode body is not polarized.

14. An electrochemical test probe comprising:
   a generally elongated, cylindrical housing;
   a generally cylindrical body of porous material disposed in said housing, and extending along at least a portion of the length thereof, said body of porous material having a tip portion which projects from said housing;
   an electrolyte retained in at least a portion of said body of porous material;
   an electrode disposed in said housing in a coaxial relationship with at least a portion of the length of said body of porous material; and
   an electrical lead in electrical communication with said body of electrode material.

15. The test probe of claim 14, wherein said lead is in electrical communication with said body of electrode material via a body of a porous, electrically conductive material.

16. The test probe of claim 15, wherein said porous, electrically conductive material comprises a foamed metal.

17. The test probe of claim 15, wherein said porous, electrically conductive body is disposed in a coaxial relationship with at least a portion of the length of the electrode.

18. The test probe of claim 14, wherein said electrode comprises a porous carbon material having a coating of a catalytic material supported thereupon.

19. The test probe of claim 18, wherein said catalytic material comprises an oxygen reduction catalyst.

20. A method for analyzing an electrochemical property of a sample of a material, said method comprising the steps of:
   providing the probe of claim 14;
   providing an electrochemical analyzer;
   coupling the lead of said probe to said analyzer;
   providing a test sample;
   establishing electrical communication between said sample and said analyzer;
   contacting said sample with the tip of said probe so as to establish electrical and ionic communication between said sample and the electrode in said probe; whereby an electrochemical cell is established wherein said sample is one electrode of said cell and said electrode body of said probe is the other electrode of said cell, said cell manifesting a detectable electrochemical property; and
   analyzing said detectable electrochemical property of said cell with said analyzer.

* * * * *